US00PP24249P3

(12) United States Plant Patent
Clark

(10) Patent No.: US PP24,249 P3
(45) Date of Patent: Feb. 18, 2014

(54) BLACKBERRY PLANT NAMED 'APF-77'

(50) Latin Name: ***Rubus* subgenus *Rubus* Watson**
Varietal Denomination: APF-77

(75) Inventor: John Reuben Clark, Fayetteville, AR (US)

(73) Assignee: The Board of Trustees of The University of Arkansas, Little Rock, AK (US)

( * ) Notice: Subject to any disclaimer, the term of this patent is extended or adjusted under 35 U.S.C. 154(b) by 98 days.

(21) Appl. No.: 13/374,444

(22) Filed: Dec. 29, 2011

(65) Prior Publication Data

US 2013/0174305 P1 Jul. 4, 2013

(51) Int. Cl.
*A01H 5/00* (2006.01)

(52) U.S. Cl.
USPC ..... Plt./203

(58) Field of Classification Search
USPC ..... Plt./203
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark et al, |
| PP11,865 | P2 | 5/2001 | Clark et al. |
| PP14,935 | P2 | 6/2004 | Clark |
| PP15,788 | P2 | 6/2005 | Clark |
| PP16,989 | P3 | 8/2006 | Clark et al. |
| PP17,162 | P3 | 10/2006 | Clark et al. |
| PP17,983 | P2 | 9/2007 | Cabrera Avalos |
| PP20,891 | P3 | 3/2010 | Clark |
| PP22,449 | P3 | 1/2012 | Clark |

OTHER PUBLICATIONS

Alisha et al. An evaluation of Fertility in Arkansas Primocane-fruiting Blackberries. HortiScience vol. 45(7) Jul. 2010.*

Clark, J.R., et al., "'APF-45'primocane-fruiting blackberry," Hort. Science (2011) 46(4):670-673.

Ruple, A., et al., "An evaluation of fertility in Arkansas primocane-fruiting blackberries," Hort. Science (2010) 45:1-6.

* cited by examiner

*Primary Examiner* — Annette Para
(74) *Attorney, Agent, or Firm* — Andrus, Sceales, Starke & Sawall, LLP

(57) ABSTRACT

Description and specifications of a new and distinct blackberry cultivar named 'APF-77' which originated from seed produced by a hand pollinated cross of APF-12 (U.S. Plant Pat. No. 16,989)×Arapaho (U.S. Plant Pat. No. 8,510) is provided. This new blackberry cultivar can be distinguished by its primocane-fruiting trait with attractive, large fruit with excellent flavor, excellent plant health, and erect canes and enhanced performance for fruit set and development in high summer temperatures.

4 Drawing Sheets

Latin name: *Rubus* subgenus *Rubus* Watson.

BACKGROUND

The new cultivar of blackberry called 'APF-77' is described herein. The new cultivar originated from a hand-pollinated cross of APF-12 (U.S. Plant Pat. No. 16,989)× Arapaho (U.S. Plant Pat. No. 8,510) made in 2001. The seeds resulting from this controlled hybridization were germinated in a greenhouse in the spring of 2002 and planted in a field near Clarksville, Ark. (West-Central Arkansas). The seedlings fruited in the summer of 2003 and one seedling, designated APF-77, was selected for its primocane-fruiting performance with attractive, large fruit with excellent flavor, excellent plant health, and erect canes.

SUMMARY OF THE INVENTION

The new and distinct cultivar of blackberry originated from a hand-pollinated cross of APF-12 (U.S. Plant Pat. No. 16,989; female)×Arapaho (U.S. Plant Pat. No. 8,510; male) made in 2001 and located near Clarksville, Ark. (West-Central Arkansas). The botanical designation of the new cultivar of blackberry is *Rubus* subgenus *Rubus* Watson.

The seeds resulting from this controlled hybridization were germinated in a greenhouse in the spring of 2002 and planted in a field near Clarksville, Ark. The seedlings fruited in the summer of 2003 on floricanes and primocanes, and one seedling, designated APF-77, was selected for its primocane-fruiting performance with attractive, large fruit with excellent flavor, excellent plant health, and erect canes.

During 2003, the original plant selection was propagated asexually from root cuttings at the above-noted location, and a test row of 40 plants was established. Subsequently, larger test plantings have been established with asexually multiplied plants at two locations in Arkansas. Additionally, the cultivar has been tested at test plots in Lincolnton, N.C., Watsonville, Calif., State College, Pa., Frankfort, Ky., and Aurora, Oreg., and at each location propagation was from root cuttings from the Clarksville, Ark. test plot.

The new cultivar has been asexually multiplied annually since 2003 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

Test plantings over a wide geographic area have shown this new cultivar to be adapted to differing soil and climatic conditions. Further, its primocane-fruiting performance is substantially better in more moderate summer climates such as Aurora, Oreg. and Watsonville, Calif., as evidenced by larger fruit weight and higher yields compared to Clarksville, Ark. However, fruit set of the new cultivar has usually been better than other primocane-fruiting blackberries when temperatures during flowering and fruit development exceeded 29.4-32.2° C. (85-90° F.). A key differentiation of the new cultivar and its parent Arapaho and most other blackberry cultivars that are floricane-fruiting is that the primocane-fruiting plant produces fruit on current-season canes (primocanes), and the portion of the cane that does not fruit in the current season will fruit the following season (floricane fruiting).

BRIEF DESCRIPTION OF THE PHOTOGRAPHS

The accompanying photographs show typical specimens of the new variety in color as nearly true as it is reasonably possible to make in a color illustration of this character. The plants in the drawings were 5 years old.

Figure 1:
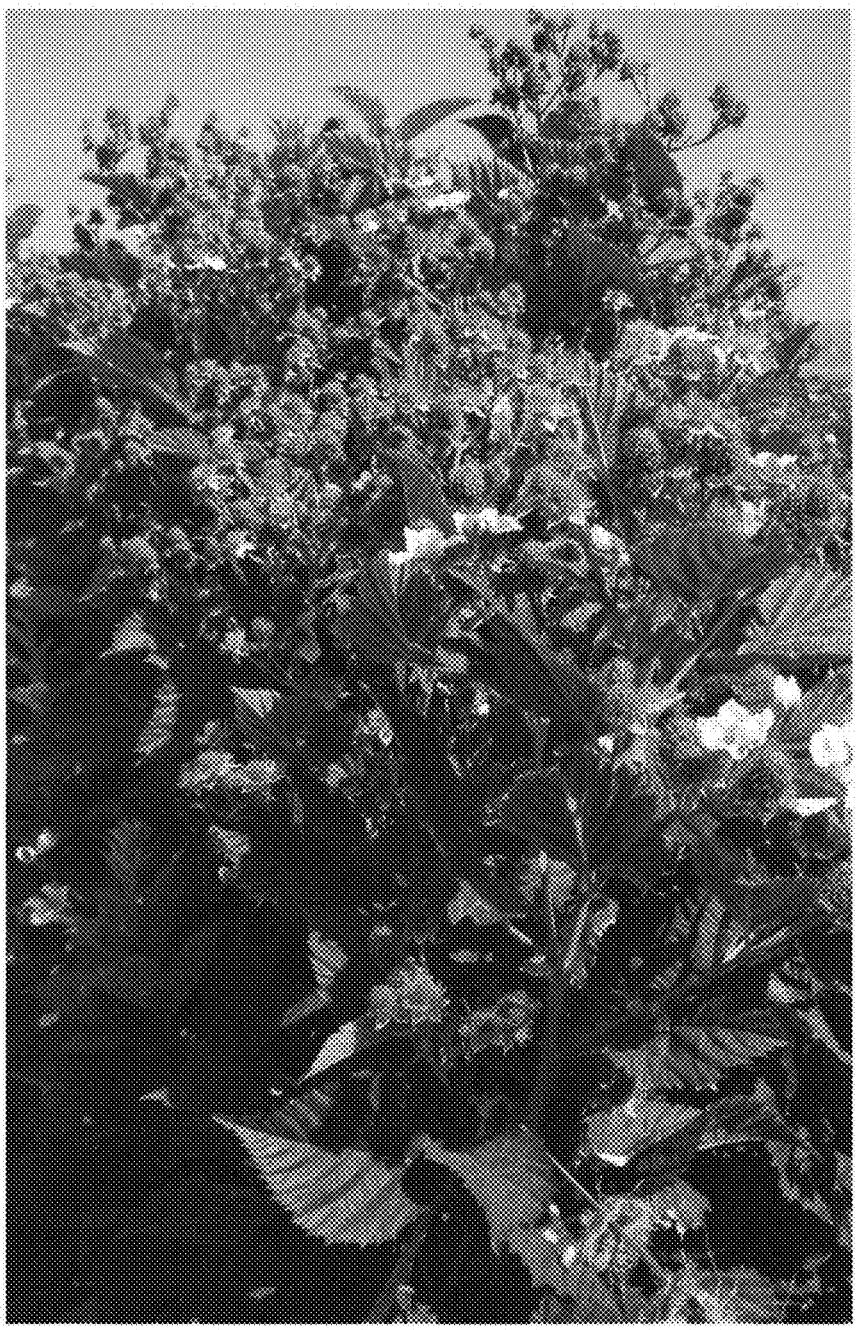
FIG. 1 is a photograph a blackberry cane of 'APF-77' in mid August showing the primocane-fruiting character with unripe, green fruit, as exemplified by flower buds at the terminus of a primocane at Watsonville, Calif.
Figure 2:
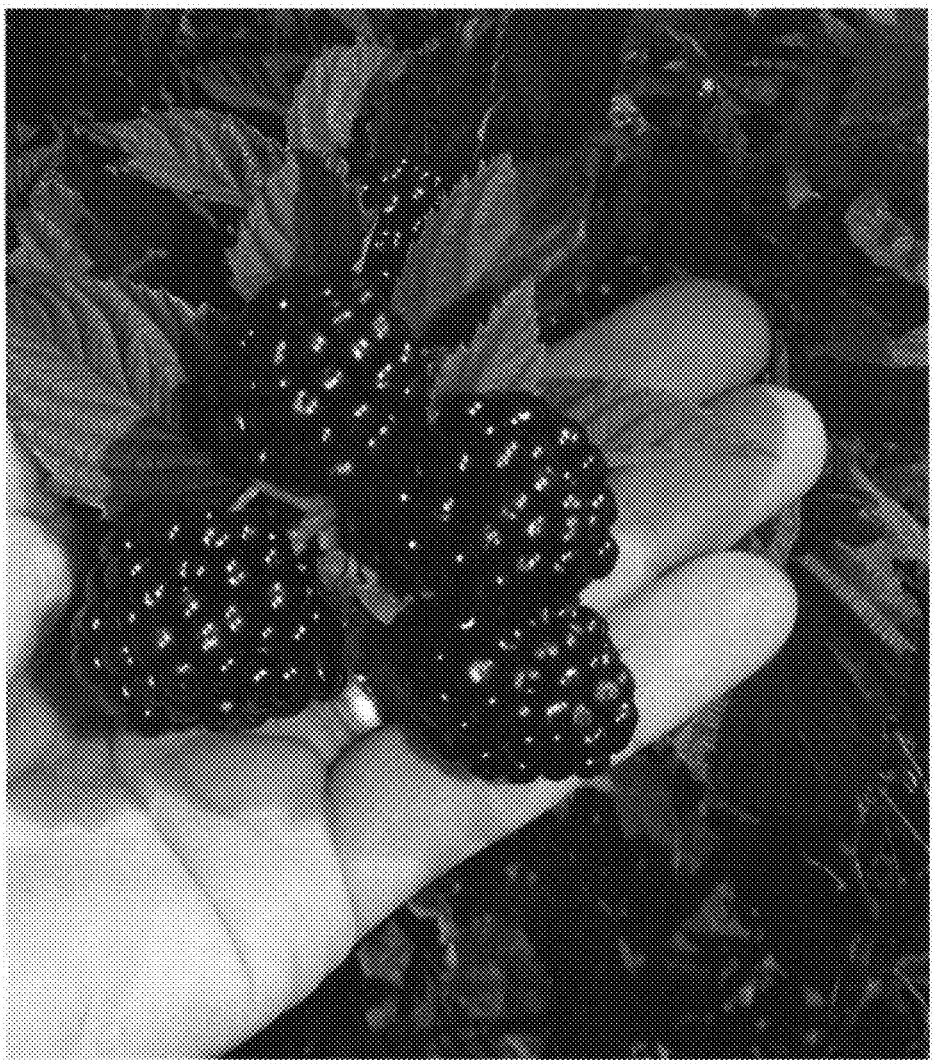
FIG. 2 is a photograph of ripe fruit on a primocane taken in early October near Clarksville, Ark.
Figure 3:
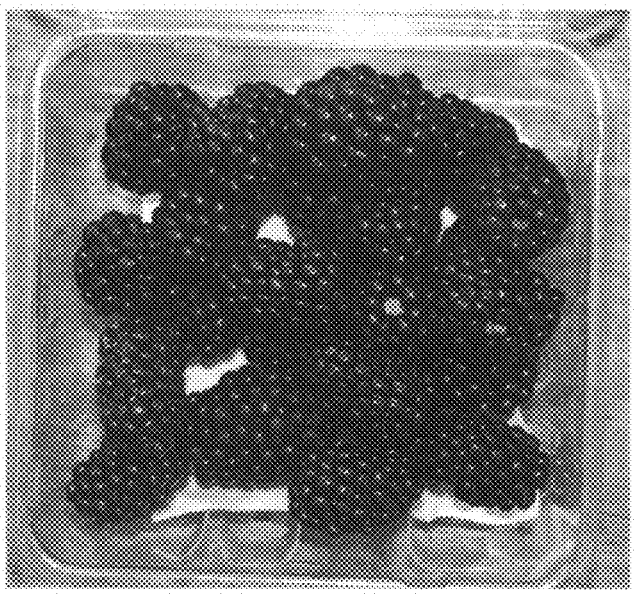

FIG. 3. is a photograph of harvested primocane fruit taken in July, near Clarksville, Ark.

Figure 4:
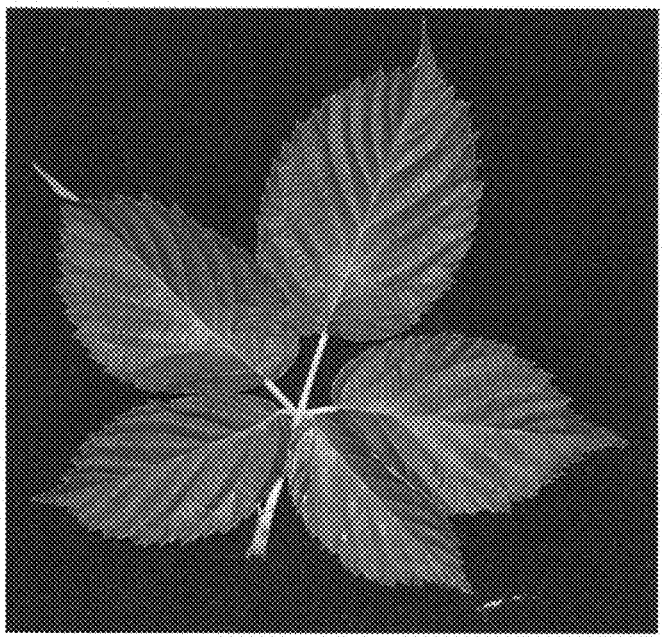

FIG. 4 is a photograph showing the adaxial side of a primocane leaf.

Figure 5:
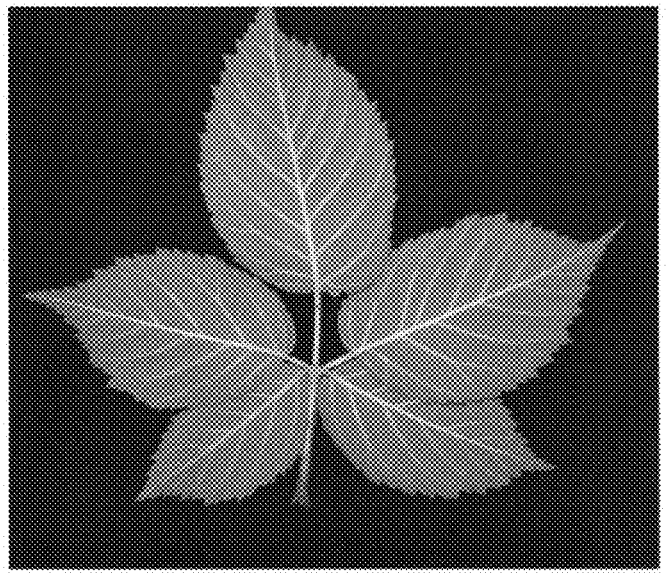

FIG. 5 is a photograph showing the abaxial side of a primocane leaf.

DETAILED DESCRIPTION OF THE NEW CULTIVAR APF-77

Plants and fruit of this new cultivar differ phenotypically from its parents. The new cultivar has better flavor and overall fruit quality, larger berry size and is more productive with more intense and consistent primocane-fruiting performance than the parent APF-12, and has the primocane-fruiting trait expression not found in parent Arapaho. Parent Arapaho is thornless while the new cultivar has thorns. Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes can be trained to a self-supporting hedgerow although it is beneficial to use a trellis with supporting wires to prevent canes from falling over due to wind or heavy fruitloads. The plants are thorny. Plants and fruit are moderately resistant to anthracnose [*Elsinoe veneta* (Burkh.) Jenkins], and plants appear immune to orange rust [*Gymnoconia nitens* (Schwein.) F. Kern and H. W. Thurston.]. No screening has been done for resistance to double blossom/rosette [*Cercosporella rubi* (Wint.) Plakidas]

The floricane and primocane bloom periods of the new cultivar begin on the same date and averages the same length as APF-12. Primocane bloom of the new cultivar has been observed to be more intense in Arkansas compared to APF-12, particularly in summer temperatures over 90° F.

Floricane fruit of the new cultivar begins ripening at the same time as APF-12 and can extend 10 days later than APF-12 due to the common emergence of basal fruiting canes providing for the more extended fruiting period. Average first ripening date is 2 June in West-Central Arkansas. The average floricane fruiting period is 40-50-days. Average first primocane fruit ripening date is 15 July in West-Central Arkansas. In Aurora, Oreg., first primocane fruit ripening date averaged Sept. 10.

Fruit yields of the new cultivar on floricanes are usually 3 to 4 kg (6.0 to 9.0 lb/plant) if the floricanes are retained for fruiting, exceeding that for APF-12, in West-Central Arkansas. Fruit yields of the cultivar on primocanes in West-Central Arkansas range from 0.2 to 1.0 kg (0.4 to 2.2 lb/plant) and exceed that of APF-12. On primocanes in Aurora, Oreg., yield averaged 3.0 kg (6.6 lb/plant), and in Watsonville, Calif. averaged 3.9 kg (8.6 lb/plant). The difference in primocane yields are believed to be due to temperatures in Oregon and California test locations being more moderate during primocane flowering and fruiting compared to West-Central Arkansas. The increased yield of the new cultivar over that of APF-12 in Arkansas is believed to be due to higher heat tolerance of flowers and fruit.

The fruit is slightly conical in shape, bright glossy black in color, and very attractive. The floricane fruit is medium-large (6-7 g/berry). Floricane fruit size of the new cultivar is maintained well throughout the entire harvest season. Primocane fruit in West-Central Arkansas of the new cultivar averaged 3.5 g/berry, while primocane fruit in Aurora, Oreg. averaged 9.1 g and in Watsonville, Calif. averaged 4.4 g. Primocane fruit size in West-Central Arkansas can be reduced in high summer temperatures (exceeding 29.4-32.2° C./85 to 90° F.) but is more uniform in the Oregon and California test sites. The new cultivar exhibits excellent fruit fertility with full drupelet set. The fruit is moderately firm at maturity, comparable to that of APF-12. Storage potential of fresh fruit of the new cultivar is not acceptable for shipping due to development of reddening of drupes, fruit softening and leakage during storage. The fresh fruit rates very good in flavor, and higher than APF-12. The flavor is sweet and mildly acidic, with a distinct blackberry aroma. The soluble solids concentration averages 10.2% on shiny black fruit, higher than APF-12 (9.1%) and has substantially reduced bitterness in the flavor profile compared to APF-12.

Floricane fruit and flower clusters are medium-large, cymose, and are mostly borne on the periphery of the plant canopy, providing easy access to harvest. Flower fertility is high and clusters are well filled.

Primocane fruit and flowers are borne on the cane terminus, and fruiting continues down the primocane during the season. Canes usually attain a length of approximately 122 cm (48 inches ft) prior to the appearance of flower buds. The number of nodes down the cane that develop flowers is largely dependent on the length and conditions of the late summer to fall growing period, particularly the field temperatures during this period.

The following is a detailed description of the botanical and pomological characteristics of the subject blackberry. Color data are presented in Royal Horticultural Society Colour Chart (1986 $2^{nd}$ edition) designations. Where dimensions, sizes, colors, and other characteristics are given, it is to be understood that such characteristics are approximations of averages set forth as accurately as practicable.

Plants used for botanical data were 3 years old and grown on a fine sandy loam soil with trickle irrigation at the Fruit Research Station near Clarksville, Ark. The plants were fertilized near budbreak (late March on average) with complete or nitrogen fertilizer, and had an additional nitrogen fertilizer application in early July. Primocanes were tipped at approximately 107 cm (42 inches), and grown in a hedgerow training system. Weeds were controlled with pre- and postemergence herbicides supplemented with mechanical weed control activities. A single application of liquid lime sulfur was applied to the plants at budbreak, but no other fungicides were used. The descriptions reported herein are from specimens grown near Clarksville, Ark. unless otherwise noted.

Plant:

*Size.*—Plants are grown in a hedgerow and primocanes tipped at approx. 107 cm (42 inches); plants in this system then range in size from approx. 107-140 cm (42-55 inches) tall and 91-102 cm (36-40 inches) wide.

*Growth habit.*—Moderate vigor, canes erect; suckers from crown and roots.

*Growth rate.*—Primocanes reach tipping height (107 cm; 42 inches) on 1 June, approximately one month after emergence.

*Productivity.*—Floricane — 3 to 4 kg (6.0 to 9.0 lb/plant), up to two times higher than APF-12. Primocane — 0.2 to 1.0 kg (0.4-2.2 lb/plant), higher than APF-12; At Aurora, Oreg. 3.0 kg (6.6 lb/plant) and Watsonville, Calif. 3.9 kg (8.6 lb/plant).

*Cold hardiness.*—Hardy to −13° C. (8° F.) or lower comparable to slightly hardier than APF-12. The low temperature of −13° C. (8° F.) was the lowest the cultivar has been exposed to and fruited successfully after this exposure.

*Canes.*—Thorny, erect. Floricane (dormant or winter cane): Cane diameter: base 0.85 cm; midpoint 0.67 cm; terminal 0.42 cm. Internode length: base 1.92 cm; midpoint 3.91 cm; terminal 2.41 cm. Floricane color: base Yellow-Green Group (146C); midpoint Yellow-Green Group (146C); terminus Yellow-Green Group (146C). Thorn-density (per 30 cm of cane length): base 19; midpoint 15.2; terminus 16.8. Thorn length (from tip of thorn to bottom of thorn base): 6.2 mm; range 8.0-3.7 mm, with non-curved thorn. Primocane (current-season cane): Cane diameter: base 1.16 cm; midpoint 0.93 cm; terminal 0.20 cm. Internode length: base 4.22 cm; midpoint 3.93 cm; terminal 0.86 cm. Primocane color: base Yellow-Green Group (146C) with some Red-Purple Group (60B); midpoint Yellow-Green Group (146C) with some Red-Purple Group (60B); terminus Yellow-Green Group (146C) with some Red-Purple Group (60B). Thorn density (per 30 cm of cane length): base 39.6; midpoint 23.8; terminus 5.5. Thorn length (from tip of thorn to bottom of thorn base): 6.22 mm; range 8.0-3.7, with non-curved thorn. Date of primocane emergence: May 1.

*Disease resistance.*—Moderate resistant to anthracnose, and plants appear immune to orange rust. No screening has been done for resistance to double blossom/rosette.

Foliage:

*Primocane.*—Leaves: large; mature compound leaf width 20.33 cm; length 19.86 cm. Leaflet: width 7.79 cm; length 13.11 cm; shape ovate with acute apex and subcordate base; margin doubly serrated, serration teeth length 0.40 cm and width 0.41 cm; pubescence is light on abaxial and adaxial surfaces; number of leaflets per compound leaf 3-5 with 5 most common. Color: base abaxial Yellow-Green Group (147B); adaxial Green Group (137A); midpoint abaxial Yellow-Green Group (147B); adaxial Green Group (137A); terminal abaxial Yellow-Green Group (147B); adaxial Green Group (137A). Petioles: length: 6.84 cm; color: Yellow-Green Group (146C); texture smooth. Petiolules: length: 2.66 cm; color: Yellow-Green Group (146D); texture smooth. Stipules: length: 1.43 cm; width: 0.18 cm; texture smooth.

*Floricane.*—Leaves: medium; mature compound leaf width 4.49 cm; length 4.38 cm. Leaflet: width 1.78 cm; length 3.09 cm; shape ovate with acuminate apex and obtuse base; margin doubly serrated, with serration teeth length 0.15 cm and width at base 0.18 cm; pubescence is absent. Number of leaflets per compound leaf is usually 3. Color: base abaxial Yellow-Green Group (146C); adaxial Yellow-Green Group (146B); midpoint abaxial Yellow-Green Group (146C); adaxial Yellow-Green Group (146B); terminal abaxial Yellow-Green Group (146C); adaxial Yellow-Green Group (146B). Petioles: Length 1.25 cm; color: Yellow-Green Group (146D); texture smooth. Petiolules: Length 0.31 cm; color: Yellow-Green Group (146D); texture smooth. Stipules: Length 0.78 cm; width: 0.15 cm; texture smooth.

Flowers:

*Floricane.*—Date of bloom: 1$^{st}$ bloom 1 April; full bloom 22 April; last bloom 1 May. Reproductive organs: Stamens — erect, numerous. Pistils — numerous. Pollen — normal, fertile, and abundant. Flower diameter: 4.41 cm. Petal size: length 2.29 cm; width 1.63 cm. Petal color: White Group (155B) and Greyed-Purple Group (186C). Average number flowers per cluster: 8.3. Average number of petals per flower: 8.5. Number of sepals per flower: 5.0. Peduncle length: 1.97 cm. Peduncle color: Yellow-Green Group (146B). Cyme type: simple cyme.

*Primocanes.*—Date of bloom: First bloom 10 June; Full bloom June 20 but bloom can extend for very long and have intermediate levels of intensity in the summer; last bloom usually when freeze occurs in late Oct. Reproductive organs: Stamens — numerous. Pistils — numerous. Pollen — fertile and abundant unless temperatures exceed 85 to 90° F. where pollen production can be reduced. Flower diameter: 3.07 cm. Petal size: Length: 1.42 cm; width: 1.42 cm. Petal color: White Group (155B) and Greyed-Purple Group (186C). Average number flowers per cluster: 6.3. Average number of petals per flower: 5.8. Number of sepals per flower: 5.2. Peduncle length: 2.91 cm. Peduncle color: Yellow-Green Group (146C). Cyme type: simple cyme.

Fruit:

*Floricane.*—Maturity: first ripe date is from 2 June extending 40-50 days. Size: medium-large, average fruit weight of 6-7 g; primary fruit 4.2 g; secondary fruit 3.5 g; tertiary fruit 3.9. Diameter of fruit at primary position on inflorescence: equator 1.99 cm; base pole 1.89 cm; terminal pole 1.51 cm. Diameter of fruit at secondary positions on inflorescence: equator 1.63 cm; base pole 1.60 cm; terminal pole 1.37 cm. Length (primary fruit): 2.55 cm. Shape: slightly conical. Color: Black Group (202A). Drupelet size: 0.44 cm. Seed (drupe): average length 3.7 mm; width 2.1 mm; dry weight 4.5 mg; color dry Greyed-Orange (164B). Soluble solids: 10.2%. pH: 3.5. Acidity: 0.50 g/100 ml expressed as citric acid. Processed quality: not evaluated for processing. Uses: Intended for home garden use along with local production that does not require fruit to be stored for periods over 2-3 days.

*Primocane.*—Maturity: Average first ripe date is 15 July and can fruit until frost depending on environment and cultural management, similar to APF-12; in Aurora, Oreg., first ripe date 10 Sept. with fruiting extending until mid October or later depending on temperature; in Watsonville, Calif. first ripe date 28 Aug. and fruiting extending until early December. Size: medium-small, ave. 3.5 g; In Aurora, Oreg. average size 9.1 g and in Watsonville, Calif. 4.4 g. Primary fruit 3.2 g; secondary fruit 3.6 g; tertiary fruit 3.7 g. Diameter of fruit at primary position on inflorescence: equator 2.03 cm; base pole 1.77 cm; terminal pole 1.43 cm. Diameter of fruit at secondary positions on inflorescence: equator 1.90 cm; base pole 1.95 cm; terminal pole 1.43 cm. Length (primary fruit): 2.55 cm. Shape: slightly conical. Color: Black Group (202A). Drupelet size: 0.44 cm. Soluble solids: 10.2%. pH: 3.7. Acidity: 0.50 g/100 ml expressed as citric acid. Processed quality: Not evaluated for processing. Uses: Intended for home garden use along with local production that does not require fruit to be stored for periods over 2-3 days.

The Cultivar: The most distinctive features of the cultivar are primocane-fruiting trait with attractive, large fruit with excellent flavor, excellent plant health, and erect canes and enhanced performance for fruit set and development in high summer temperatures.

I claim:

1. A new and distinct cultivar of blackberry plant named 'APF-77,' substantially as illustrated and described.

* * * * *